United States Patent [19]

Smith

[11] 4,165,325

[45] Aug. 21, 1979

[54] 11-DEOXY-TRANS-4,5,13,14-TETRADEHYDRO-PGI$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 915,348

[22] Filed: Jun. 14, 1978

Related U.S. Application Data

[63] Continuation-in-part of Ser. No. 821,536, Aug. 3, 1977.

[51] Int. Cl.$^2$ ............................................. C07D 307/93
[52] U.S. Cl. ............................... 260/346.22; 542/418; 542/421; 542/422; 542/426; 260/346.73
[58] Field of Search .................... 260/346.22, 346.73; 542/426, 418, 421, 422

[56] References Cited

PUBLICATIONS

Fried et al., Proc. Natl. Acad. Sci. 74, 2199 (1977).

*Primary Examiner*—John M. Ford
*Assistant Examiner*—Bernard Dentz
*Attorney, Agent, or Firm*—Robert A. Armitage

[57] ABSTRACT

The present invention relates to certain structural and pharmacological analogs of prostacyclin (PGI$_2$) which are 11-deoxy-trans-4,5,13,14-tetradehydro-PGI$_1$ compounds. These novel pharmacological agents are useful as smooth muscle stimulators.

72 Claims, No Drawings

11-DEOXY-TRANS-4,5,13,14-TETRADEHYDRO-PGI₁ COMPOUNDS

CROSS REFERENCE TO RELATED APPLICATION

The present application is a continuation-in-part of Ser. No. 821,536, filed Aug. 3, 1977, now pending.

The present invention relates to prostacyclin analogs, for which the essential material constituting disclosure therefor is incorporated by reference here from Ser. No. 821,541, filed Aug. 3, 1977, now U.S. Pat. No. 4,109,082, issued Aug. 22, 1978.

I claim:
1. A prostacyclin analog of the formula

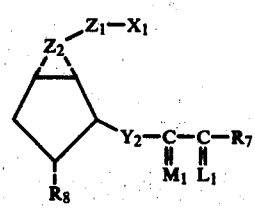

wherein $Y_2$ is $-C\equiv C-$;
wherein $Z_2$ is

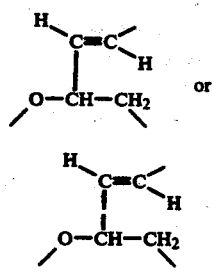 (1)

or (2)

wherein $Z_1$ is
 (1) $-(CH_2)_g-CH_2-CH_2-$, or
 (2) $-(CH_2)_g-CH_2-CF_2-$, wherein g is the integer zero, one, or 2; wherein $R_8$ is hydrogen or hydroxymethyl; wherein $M_1$ is

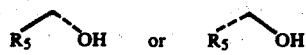

wherein $R_5$ is hydrogen or alkyl with one to 4 carbon atoms, inclusive,
wherein $L_1$ is

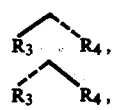

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein $X_1$ is
 (1) $-COOR_1$ wherein $R_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

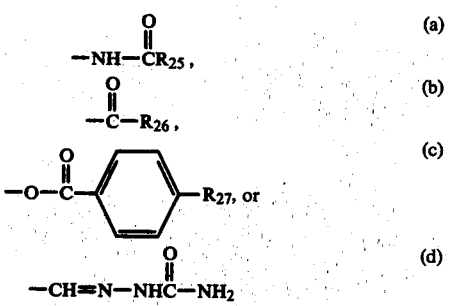

wherein $R_{25}$ is methyl, phenyl, acetamidophenyl, benzamidophenyl, or $-NH_2$; $R_{26}$ is methyl, phenyl, $-NH_2$, or methoxy; and $R_{27}$ is hydrogen or acetamido; inclusive, phenacyl, i.e.,

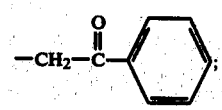

phenacyl substituted in the para position by chloro, bromo, phenyl, or benzamido; or a pharmacologically acceptable cation;
 (2) $-CH_2OH$;
 (3) $-CH_2NL_2L_3$, wherein $L_2$ and $L_3$ are hydrogen or alkyl of one to 4 carbon atoms inclusive or
 (4) $-COL_4$, wherein $L_4$ is
  (a) amino of the formula $-NR_{21}R_{22}$; wherein $R_{21}$ and $R_{22}$ are hydrogen; alkyl of one to 12 carbon atoms, inclusive; cycloalkyl of 3 to 10 carbon atoms, inclusive aralkyl of 7 to 12 carbon atoms, inclusive; phenyl; phenyl substituted with one, 2, or 3 chloro, alkyl of one to 3 carbon atoms, inclusive: hydroxy, carboxy, alkoxycarbonyl of one to 4 carbon atoms, inclusive, or nitro; carboxyalkyl of one to 4 carbon atoms, inclusive, carbamoylalkyl of one to 4 carbon atoms, inclusive; cyanoalkyl of one to 4 carbon atoms, inclusive: acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive; or nitro; pyridyl; pyridyl substituted by one, 2, or 3 chloro, alkyl of one to 3 carbon atoms, inclusive, or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms, inclusive, hydroxy, or alkoxy of one to 3 carbon atoms, inclusive; hydroxyalkyl of one to 4 carbon atoms, inclusive; dihydroxylakyl of one to 4 carbon atoms, and trihydroxyalkyl of one to 4 carbon atoms; with the further proviso that not more than one of $R_{21}$ and $R_{22}$ is other than hydrogen or alkyl;

(b) cycloamino selected from the group consisting of

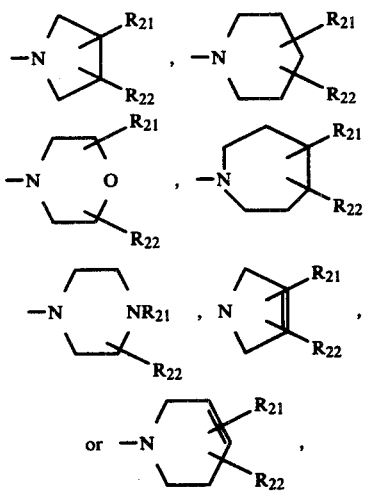

wherein $R_{21}$ and $R_{22}$ are as defined above;

(c) carbonylamino of the formula $-NR_{23}COR_{21}$, wherein $R_{23}$ is hydrogen or alkyl of one to 4 carbon atoms and $R_{21}$ is as defined above;

(d) sulfonylamino of the formula $-NR_{23}SO_2R_{21}$, wherein $R_{21}$ and $R_{23}$ are as defined above; or (e) hydrazino of the formula $-NR_{23}R_{24}$, wherein $R_{23}$ is as defined above and $R_{24}$ is amino of the formula $-NR_{21}R_{22}$, as defined above, or cycloamino, as defined above;

wherein $R_7$ is (1) $-(CH_2)_m-CH_3$, (2)

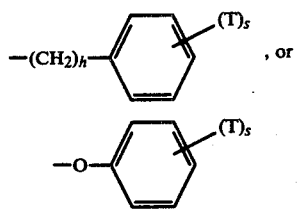

, or (3)

wherein m is the integer one to 5, inclusive, h is the integer zero to 3 inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl; and the pharmacologically acceptable acid addition salts thereof when $Z_1$ is $-CH_2NL_2L_3$.

2. A prostacyclin analog according to claim 1, wherein $R_8$ is hydroxymethyl.

3. A prostacyclin analog according to claim 2, wherein $Z_2$ is a mixture of

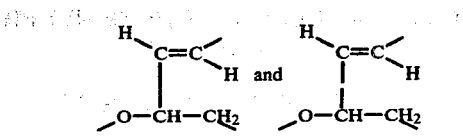

4. trans-4,5,13,14-Tetradehydro-(6RS)-11-deoxy-11α-hydroxymethyl-PGI$_1$, a prostacyclin analog according to claim 3.

5. A prostacyclin analog according to claim 2, wherein $Z_2$ is

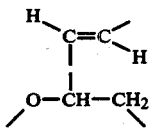

6. trans-4,5,13,14-Tetradehydro-6α-11-deoxy-11α-hydroxymethyl-PGI$_1$, a prostacyclin analog according to claim 5.

7. 15-Methyl-trans-4,5,13,14-tetradehydro-6α-11-deoxy-11α-hydroxymethyl-PGI$_1$, a prostacyclin analog according to claim 5.

8. 16,16-Dimethyl-trans-4,5,13,14-tetradehydro-6α-11-deoxy-11α-hydroxymethyl-PGI$_1$, a prostacyclin analog according to claim 5.

9. 16,16-Difluoro-trans-4,5,13,14-tetrahydro-6α-11-deoxy-11α-hydroxymethyl-PGI$_1$, a prostacyclin analog according to claim 5.

10. A prostacyclin analog according to claim 2, wherein $Z_2$ is

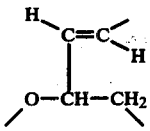

11. A prostacyclin analog according to claim 10, wherein $Z_1$ is $-(CH_2)_g-CH_2-CF_2-$.

12. 2,2-Difluoro-trans-4,5,13,14-tetradehydro-6β-11-deoxy-11α-hydroxymethyl-PGI$_1$, a prostacyclin analog according to claim 11.

13. A prostacyclin analog according to claim 10, wherein $Z_1$ is $-(CH_2)_g-CH_2-CH_2-$.

14. A prostacyclin analog according to claim 13, wherein g is zero.

15. A prostacyclin analog according to claim 14, wherein $R_7$ is

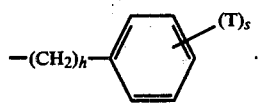

16. 17-Phenyl-18,19,20-trinor-trans-4,5,13,14-tetradehydro-6β-11-deoxy-11α-hydroxymethyl-PGI$_1$, a prostacyclin analog according to claim 15.

17. A prostacyclin analog according to claim 14, wherein $R_7$ is

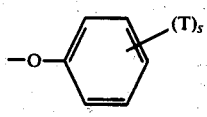

18. 16-Phenoxy-17,18,19,20-tetranor-trans-4,5,13,14-tetradehydro-6β-11-deoxy-11α-hydroxymethyl-PGI₁, a prostacyclin analog according to claim 17.

19. A prostacyclin analog according to claim 14, wherein $R_7$ is $-(CH_2)_m-CH_3-$.

20. A prostacyclin analog according to claim 19, wherein m is 3.

21. A prostacyclin analog according to claim 20, wherein $X_1$ is $-COL_4$.

22. trans-4,5,13,14-Tetradehydro-6β-11-deoxy-11α-hydroxymethyl-PGI₁ amide, a prostacyclin analog according to claim 21.

23. A prostacyclin analog according to claim 20, wherein $X_1$ is $CH_2OH-$.

24. 2-Decarboxy-2-hydroxymethyl-trans-4,5,13,14-tetradehydro-6β-11-deoxy-11α-hydroxymethyl-PGI₁, a prostacyclin analog according to claim 23.

25. A prostacyclin analog according to claim 20, wherein $X_1$ is $-COOR_1$.

26. A prostacyclin analog according to claim 25, wherein $R_5$ is methyl.

27. 15-Methyl-trans-4,5,13,14-tetradehydro-6β-11-deoxy-11α-hydroxymethyl-PGI₁, a prostacyclin analog according to claim 26.

28. A prostacyclin analog according to claim 25, wherein $R_5$ is hydrogen.

29. A prostacyclin analog according to claim 28, wherein at least one of $R_3$ and $R_4$ is fluoro.

30. 16,16-Difluoro-trans-4,5,13,14-tetradehydro-6β-11-deoxy-11α-hydroxymethyl-PGI₁, a prostacyclin analog according to claim 29.

31. A prostacyclin analog according to claim 28, wherein at least one of $R_3$ and $R_4$ is methyl.

32. 16,16-Dimethyl-trans-4,5,13,14-tetradehydro-6β-11-deoxy-11α-hydroxymethyl-PGI₁, a prostacyclin analog according to claim 31.

33. A prostacyclin analog according to claim 28, wherein $R_3$ and $R_4$ are both hydrogen.

34. trans-4,5,13,14-Tetradehydro-6β-11-deoxy-11α-hydroxymethyl-PGI₁, methyl ester, a prostacyclin analog according to claim 33.

35. trans-4,5,13,14-Tetradehydro-6β-11-deoxy-11α-hydroxymethyl-PGI₁, tris(hydroxymethyl)amino methane salt, a prostacyclin analog according to claim 33.

36. trans-4,5,13,14-Tetradehydro-6β-11-deoxy-11α-hydroxymethyl-PGI₁, adamantanamine salt, a prostacyclin analog according to claim 33.

37. trans-4,5,13,14-Tetradehydro-6β-11-deoxy-11α-hydroxymethyl-PGI₁, a prostacyclin analog according to claim 33.

38. A prostacyclin analog according to claim 1, wherein $R_8$ is hydrogen.

39. A prostacyclin analog according to claim 38, wherein $Z_2$ is a mixture of

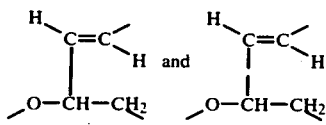

40. trans-4,5,13,14-Tetradehydro-(6RS)-11-deoxy-PGI₁, a prostacyclin analog according to claim 39.

41. A prostacyclin analog according to claim 38, wherein $Z_2$ is

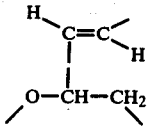

42. trans-4,5,13,14-Tetradehydro-6α-11-deoxy-PGI₁, a prostacyclin analog according to claim 41.

43. 15-Methyl-trans-4,5,13,14-tetradehydro-6α-11-deoxy-PGI₁, a prostacyclin analog according to claim 41.

44. 16,16-Dimethyl-trans-4,5,13,14-tetradehydro-6α-11-deoxy-PGI₁, a prostacyclin analog according to claim 41.

45. A prostacyclin analog according to claim 38, wherein $Z_2$ is

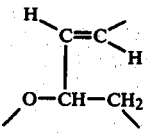

46. A prostacyclin analog according to claim 45, wherein $Z_1$ is $-(CH_2)_g-CH_2-CF_2-$.

47. 2,2-Difluoro-trans-4,5,13,14-tetradehydro-6β-11-deoxy-PGI₁, a prostacyclin analog according to claim 46.

48. A prostacyclin analog according to claim 45, wherein $Z_1$ is $-(CH_2)_g-CH_2-CH_2-$.

49. A prostacyclin analog according to claim 48, wherein g is zero.

50. A prostacyclin analog according to claim 49, wherein $R_7$ is

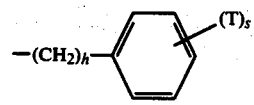

51. 17-Phenyl-18,19,20-trinor-trans-4,5,13,14-tetradehydro-6β-11-deoxy-PGI₁, a prostacyclin analog according to claim 50.

52. A prostacyclin analog according to claim 49, wherein $R_7$ is

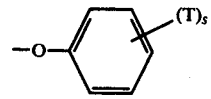

53. 16-Phenoxy-17,18,19,20-tetranor-trans-4,5,13,14-tetradehydro-6β-11-deoxy-PGI₁, a prostacyclin analog according to claim 52.

54. A prostacyclin analog according to claim 49, wherein $R_7$ is $-(CH_2)_m-CH_3-$.

55. A prostacyclin analog according to claim 54, wherein m is 3.

56. A prostacyclin analog according to claim 55, wherein $X_1$ is $-COL_4$.

57. trans-4,5,13,14-Tetradehydro-6β-11-deoxy-PGI$_1$ amide, a prostacyclin analog according to claim 56.

58. A prostacyclin analog according to claim 55, wherein X$_1$ is CH$_2$OH-.

59. 2-Decarboxy-2-hydroxymethyl-trans-4,5,13,14-tetradehydro-6β-11-deoxy-PGI$_1$, a prostacyclin analog according to claim 58.

60. A prostacyclin analog according to claim 55, wherein X$_1$ is -COOR$_1$.

61. A prostacyclin analog according to claim 60, wherein R$_5$ is methyl.

62. 15-Methyl-trans-4,5,13,14-tetradehydro-6β-11-deoxy-PGI$_1$, a prostacyclin analog according to claim 61.

63. A prostacyclin analog according to claim 60, wherein R$_5$ is hydrogen.

64. A prostacyclin analog according to claim 63, wherein at least one of R$_3$ and R$_4$ is fluoro.

65. 16,16-Difluoro-trans-4,5,13,14-tetradehydro-6β-11-deoxy-PGI$_1$, a prostacyclin analog according to claim 64.

66. A prostacyclin analog according to claim 63, wherein at least one of R$_3$ and R$_4$ is methyl.

67. 16,16-Dimethyl-trans-4,5,13,14-tetradehydro-6β-11-deoxy-PGI$_1$, a prostacyclin analog according to claim 66.

68. A prostacyclin analog according to claim 63, wherein R$_3$ and R$_4$ are both hdrogen.

69. trans-4,5,13,14-Tetradehydro-6β-11-deoxy-PGI$_1$, methyl ester, a prostacyclin analog according to claim 68.

70. trans-4,5,13,14-Tetradehydro-6β-11-deoxy-PGI$_1$, tris-(hydroxymethyl)amino methane salt, a prostacyclin analog according to claim 68.

71. trans-4,5,13,14-Tetradehydro-6β-11-deoxy-PGI$_1$, adamantanamine salt, a prostacyclin analog according to claim 68.

72. trans-4,5,13,14-Tetradehydro-6β-11-deoxy-PGI$_1$, a prostacyclin analog according to claim 68.

* * * * *